US008367044B2

(12) United States Patent
Yoshida et al.

(10) Patent No.: US 8,367,044 B2
(45) Date of Patent: Feb. 5, 2013

(54) SUNSCREEN COSMETIC

(75) Inventors: Susumu Yoshida, Yokohama (JP); Koji Abe, Yokohama (JP); Hideto Ueda, Yokohama (JP); Yuki Sugiyama, Yokohama (JP); Tomiko Takakura, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/388,446

(22) PCT Filed: Jul. 26, 2010

(86) PCT No.: PCT/JP2010/062505
§ 371 (c)(1),
(2), (4) Date: Apr. 15, 2012

(87) PCT Pub. No.: WO2011/027632
PCT Pub. Date: Mar. 10, 2011

(65) Prior Publication Data

US 2012/0195841 A1 Aug. 2, 2012

(30) Foreign Application Priority Data

Sep. 1, 2009 (JP) ................................ 2009-201278

(51) Int. Cl.
*A61K 8/00* (2006.01)
*A61K 9/00* (2006.01)
*A61K 8/02* (2006.01)
*A61Q 17/04* (2006.01)

(52) U.S. Cl. .......................... 424/60; 424/400; 424/401

(58) Field of Classification Search .................... 424/60, 424/400, 401
See application file for complete search history.

(56) References Cited

U.S. PATENT DOCUMENTS 7,811,594 B2 * 10/2010 Schreiber et al. ............. 424/401
2005/0118211 A1 * 6/2005 Nakamura et al. ............ 424/401

FOREIGN PATENT DOCUMENTS

JP 10-279456 A 10/1998
JP 2001-342451 A 12/2001

OTHER PUBLICATIONS

International Search Report issued on Oct. 19, 2010 in counterpart International Application No. PCT/JP2010/062505.

* cited by examiner

*Primary Examiner* — Mina Haghighatian
*Assistant Examiner* — Luke Karpinski
(74) *Attorney, Agent, or Firm* — Andrew F. Young, Esq.; Lackenbach Siegel, LLP

(57) ABSTRACT

The present invention provides a sunscreen cosmetic comprising, relative to the total amount of the sunscreen cosmetic, 10-90 wt % of agar microgel (wherein the agar content in the agar microgel is 0.4-1 wt %) and 0.1-5 wt % of a water soluble ultraviolet absorbent.

It was necessary to blend in an organic ultraviolet absorbent and such to give sunscreen cosmetics a high SPF value. However, there was a problem in that it was hard for a water soluble ultraviolet absorbent in the formulation to achieve the expected SPF function. Also, sunscreen cosmetics are particularly desired to give a freshing texture upon use.

In view of the fact that a high blend ratio of an oil soluble ultraviolet absorbent inhibits the freshing texture upon use, the object of the present invention is to provide a sunscreen cosmetic that achieves a high SPF value and a freshing texture upon use by mainly blending in a water soluble ultraviolet absorbent.

9 Claims, 2 Drawing Sheets

SUNSCREEN COSMETIC

CROSS REFERENCE TO A RELATED APPLICATIONS

This is a national stage patent application of co-pending PCT International application No. PCT/JP2010/062505, filed Jul. 26, 2010.

TECHNICAL FIELD

The present invention relates to a sunscreen cosmetic. It specifically relates to a sunscreen cosmetic that secures a high SPF value and achieves a freshing texture upon use by effectively adding a water soluble ultraviolet absorbent. It is not necessary to blend in an oil soluble ultraviolet absorbent in the sunscreen cosmetic of the present invention.

BACKGROUND ART

It was necessary to blend in an organic ultraviolet absorbent and such to give sunscreen cosmetics a high SPF value. For the organic ultraviolet absorbent to be blended into the ultraviolet absorbent, there are oil soluble ultraviolet absorbents and water soluble ultraviolet absorbents. The water soluble ultraviolet absorbents had a problem in that, compared with the oil soluble ultraviolet absorbents, they were less likely to fully achieve the expected SPF function. Therefore, the oil soluble ultraviolet absorbents are often blended into sunscreen cosmetics and, even when water soluble ultraviolet absorbents are blended in, generally the oil soluble ultraviolet absorbents are also blended in.

On the other hand, sunscreen cosmetics are particularly desired to give a freshing texture upon use. However, when the oil soluble ultraviolet absorbents are blended in, compared with the water soluble ultraviolet absorbents, the sunscreen cosmetic's tactile sensation upon use becomes oily and the important freshing texture is lost.

When blending an oil soluble ultraviolet absorbent into a sunscreen cosmetic, it is common to adopt a formulation form of emulsion such as an oil-in-water emulsified composition or a water-in-oil emulsified composition. That is, if an oil soluble ultraviolet absorbent is to be blended in, the formulation form is limited to an emulsion.

Also, Patent Document 1 reports that, as technology for securing the tactile sensation upon use and the stability of a sunscreen cosmetic, and particularly for sunscreen cosmetics made of an oil-in-water emulsified composition, a thickener obtained by microgelation of a hydrophilic compound having a high gelating ability, such as agar, contributes highly to the usability and stability of the cosmetic.

And, as reported in Patent Documents 2-4, a technology is known in which, for oil-in-water emulsified composition sunscreen cosmetics having fine particles of an ultraviolet scattering agent such as titanium oxide and zinc oxide dispersed in the inner oil phase, a common thickener such as succinoglucane, xanthan gum, and acrylamide is blended in to thicken the system and stably disperse not only the emulsified particles but the fine particles into the water phase.

Patent Document 5 provides an oil-in-water emulsified sunscreen cosmetic that does not have a high blend ratio of an oil soluble ultraviolet absorbent, achieves both the ultraviolet protection effect and stability without sacrificing a freshing texture upon use, and provides superior uniformity of the coating film and usability (absorption into the skin). Although Patent Document 5 has a one-line description of agar as the thickener for the potential ingredients, it has no description of the augmentation of the ultraviolet absorption effect of a water soluble ultraviolet absorbent by means of an agar microgel as achieved by the present invention. Furthermore, the invention of Patent Document 5 also contains an oil soluble ultraviolet absorbent.

Also, Patent Document 6 discloses an oil-in-water emulsified composition sunscreen cosmetic that contains both phenylbenzimidazole sulfonic acid, as a water soluble ultraviolet absorbent, and an oil soluble ultraviolet absorbent together. However, similarly to Patent Document 5, there is no description or suggestion of the unpredictable effect of increasing the ultraviolet absorption of the water soluble ultraviolet absorbent by means of an agar microgel as achieved in the present invention. Also, this document does not describe any extreme restriction of the blend ratio of the oil soluble ultraviolet absorbent or not blending in thereof.

PRIOR ART DOCUMENTS

Patent Documents

Patent Document 1: Japanese Patent No. 3531735
Patent Document 2: JP 2004-210698 A
Patent Document 3: JP 2005-225771 A
Patent Document 4: JP 2005-247722 A
Patent Document 5: JP 2008-162930 A
Patent Document 6: WO 2007/122822

SUMMARY OF INVENTION

Problem that Invention is to Solve

It was necessary to blend high amount of organic ultraviolet absorbent in the formulation in order to give sunscreen cosmetics a high SPF value. For the organic ultraviolet absorbent, there are oil soluble ultraviolet absorbents and water soluble ultraviolet absorbents; there was a problem in that it is difficult to achieve the sufficient SPF function expected of the formulation if only the water soluble ultraviolet absorbents are used.

On the other hand, sunscreen cosmetics are particularly desired to give a freshing texture upon use. In view of the fact that the addition of an oil soluble ultraviolet absorbent inhibits a freshing texture upon use, and also in view of the fact that in such case the formulation is also limited to an emulsified composition, the object of the present invention is to achieve a high SPF value by mainly blending in a water soluble ultraviolet absorbent as the organic ultraviolet absorbent and thus provide a sunscreen cosmetic that also achieves a freshing texture upon use.

Technical Solution

That is, the present invention provides a sunscreen cosmetic comprising, relative to the total amount of the sunscreen cosmetic, 10-90 wt % of agar microgel (wherein the agar content in the agar microgel is 0.4-1 wt %) and 0.1-5 wt % of a water soluble ultraviolet absorbent.

Furthermore, the present invention provides the aforementioned sunscreen cosmetic wherein said water soluble ultraviolet absorbent is phenylbenzimidazole sulfonic acid and/or 2-hydroxy-4-methoxybenzophenonsulfonic acid.

Furthermore, the present invention provides the aforementioned sunscreen cosmetic comprising, relative to the total amount of the sunscreen cosmetic, 1 wt % or less oil soluble ultraviolet absorbent.

Also, the present invention provides the aforementioned sunscreen cosmetic wherein no substantial amount of an oil soluble ultraviolet absorbent is blended in.

Furthermore, the present invention provides a method of manufacturing a sunscreen cosmetic in which the agar gel used is obtained by dissolving agar in water while stirring and heating are conducted, followed by cooling, the agar content in the agar gel is 0.4-1 wt %, after the dissolution and cooling said agar microgel is crushed with a homomixer down to approximately 10-400 micrometers to obtain an agar microgel, and then a sunscreen cosmetic is manufactured by blending, relative to the total amount of the sunscreen cosmetic, 10-90 wt % of the obtained agar microgel and, relative to the total amount of the sunscreen cosmetic, 0.1-5 wt % of a water soluble ultraviolet absorbent into the cosmetic base agent.

Advantageous Effects (1) The sunscreen cosmetic of the present invention has a high ultraviolet absorption capacity. The inventors discovered that the agar microgel surprisingly increases the ultraviolet absorption effect of the water soluble ultraviolet absorbent. As a result, the inventors made it possible to provide a sunscreen cosmetic that has a high ultraviolet absorption effect by using a water soluble ultraviolet absorbent. This invention is fundamentally different from a conventional method that increases the ultraviolet absorption effect by increasing the blend ratio of the water soluble ultraviolet absorbent; that is, this is an invention in which the agar microgel functions as the ultraviolet absorption effect enhancer for the water soluble ultraviolet absorbent.

(2) It is not necessary to blend in an oil soluble ultraviolet absorbent to achieve a high ultraviolet absorption effect. Even if it is desirable to blend in an oil soluble ultraviolet absorbent for some reason, the blend ratio, relative to the total amount of the sunscreen cosmetic, should preferably be 1 wt % or less. In this range a freshing texture upon use is secured. There is no need to blend in an oil soluble ultraviolet absorbent in the present invention. It is also an effect of the present invention that the oil soluble ultraviolet absorbent's blend ratio is very limited, i.e. 1 wt % or less, or just zero.

(3) The sunscreen cosmetic of the present invention gives a freshing texture upon use.

(4) The sunscreen cosmetic of the present invention is not limited in terms of its formulation form to oil-in-water emulsified compositions or water-in-oil emulsified compositions; it can be used also for sunscreen cosmetics in an aqueous solution form. This would manifest an even more freshing texture upon use.

MODE FOR CARRYING OUT THE INVENTION

Figure 1:
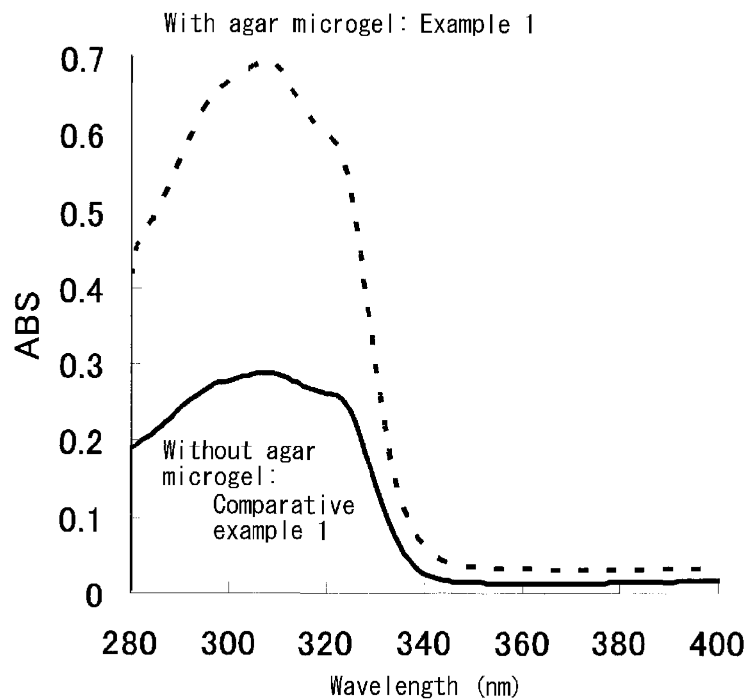
FIG. 1 is an ultraviolet absorption spectrum showing that an agar microgel increases the ultraviolet absorption effect. The water soluble ultraviolet absorbent is phenylbenzimidazole sulfonic acid.

The present invention is described in detail below.

<Agar Microgel>

In the present invention, an agar microgel stands for solidified agar crushed into the micrometers order. For the agar, any natural or commercial product can be used without limitations as long as agarose that has a high gelating capability is the main ingredient. For the commercially available agar, for example, Ina agar PS-84, Z-10, AX-30, AX-100, AX-200, T-1, S-5, and M-7 (from Ina Food Industry, Co., Ltd.) can be used preferably. Purified agarose can be also be used for said agar.

Next, preparation of the agar microgel is described. The agar microgel used in the present invention can be prepared according to a conventional method.

That is, agar is dissolved in water or a water-based ingredient, which is then left alone and cooled to form gel. Agar can be dissolved in water or a water-based ingredient by mixing, heating and such.

Gelation (solidification) is done by stopping the heating after the dissolution and leaving the mixture alone until the temperature is lower than the gelation temperature (solidification temperature).

Selection of the water-based ingredient used together with water is not limited in particular as long as it is a water-based ingredient that can be used in the cosmetic or medical drug field; examples include glycols such as 1,3-butylene glycol and propylene glycol, as well as ingredients commonly used as a water phase ingredient in cosmetics. Specific examples include, but are not limited to, chelating agents such as metaphosphates and edetates, pH adjusting agents, and preservatives.

Preferable is an agar microgel obtained by dissolving agar in water while stirring and heating are conducted, followed by cooling, wherein the agar content in the agar gel is 0.4-1 wt %; after the dissolution and cooling said agar microgel is crushed with a homomixer down to approximately 10-400 micrometers to obtain an agar microgel.

The degree of crushing can be adjusted according to the purpose as long as the particle size of the obtained microgel is within said range. When smoother usability is required, a microgel having a finer particle size is prepared by thorough crushing by high speed stirring; on the other hand, when the tactile sensation of the microgel itself is required, the degree of crushing is lessened by light stirring to obtain a microgel having a relatively large particle size.

In the present invention, it is particularly preferable to prepare the microgel to have an average particle size of 10-400 micrometers.

The viscosity of the microgel thus obtained can be adjusted appropriately for the cosmetic product into which it is to be blended; a preferable viscosity is 2,000-1,000,000 mPa·s as measured with a B-type viscometer (rotational speed 0.6 rpm, 25° C.) when the agar concentration, relative to water or the water-based ingredient, is 0.5-2%.

The agar concentration in the agar microgel is preferably 0.2-1.5 wt %, more preferably 0.4-1 wt %, in water or in the water-based ingredient.

The blend ratio of the agar microgel in the sunscreen cosmetic is, relative to the total amount of the sunscreen cosmetic, preferably 10-90 wt %, and more preferably 30-80 wt %. This increases the ultraviolet absorption effect of the water soluble ultraviolet absorbent.

<Water Soluble Ultraviolet Absorbent>

The water soluble ultraviolet absorbent used in the present invention is phenylbenzimidazole sulfonic acid and/or 2-hydroxy-4-methoxybenzophenonsulfonic acid. The phenomenon of a dramatic increase in the ultraviolet absorption effect of the ultraviolet absorbent due to an agar microgel is an amazing fact demonstrated by the inventors.

Phenylbenzimidazole sulfonic acid and/or 2-hydroxy-4-methoxybenzophenonsulfonic acid are prior art water soluble ultraviolet absorbents; they can be used in the acid form or in the salt form that are commercially available. When using the acid form such as phenylbenzimidazole sulfonic acid and 2-hydroxy-4-methoxybenzophenonsulfonic acid, a neutralizer is required; examples of such a neutralizer include sodium hydroxide, potassium hydroxide, and triethanolamine.

The blend ratio of the water soluble ultraviolet absorbent is, relative to the total amount of the sunscreen cosmetic, preferably 0.1-5 wt %, more preferably 0.3-3 wt %.

In the present invention, there is no need to blend in an oil soluble ultraviolet absorbent. If it is to be blended in for some reason, the blend ratio would be 1 wt % or less relative to the total amount of the sunscreen cosmetic. Selection of the oil soluble ultraviolet absorbent is not limited; it is acceptable to blend in octylmethoxy cinnamate in the amount of 0.1-1 wt % or less. In terms of a freshing texture upon use, the lesser the blend ratio of the oil soluble ultraviolet absorbent the better; the most preferable is not to blend it in at all.

The sunscreen cosmetic of the present invention is completed just by blending the aforementioned essential ingredients in a sunscreen cosmetic base agent. That is, the agar gel used is obtained by dissolving agar in water while stirring and heating are conducted, followed by cooling, the agar content in the agar gel is 0.4-1 wt %, said agar microgel is crushed with a homomixer down to approximately 10-400 micrometers to obtain an agar microgel, and then a sunscreen cosmetic can be prepared by blending in, relative to the total amount of the sunscreen cosmetic, 10-90 wt % of the obtained agar microgel and also blending in, relative to the total amount of the sunscreen cosmetic, 0.1-5 wt % of a water soluble ultraviolet absorbent. As described above, the present invention allows easy preparation, without a complex preparation method, of a sunscreen cosmetic that increases the ultraviolet absorption effect of the water soluble ultraviolet absorbent and gives a freshing texture upon use, which is another point that contributes to the inventiveness of the present invention.

In addition to the aforementioned ingredients, other ingredients used in external preparations such as cosmetics and drugs can be blended as necessary into the sunscreen cosmetic of the present invention as long as the purpose/effect of the present invention is not adversely affected; examples include fats and oils, waxes, hydrocarbon oils, higher fatty acids, higher alcohols, synthetic ester oils, silicone oils, water soluble polymers, chelating agents, lower alcohols, polyhydric alcohols, pH adjusting agents, antioxidants, powders, perfumes, and water. However, the examples are not limited to those shown.

The formulation form of the sunscreen cosmetic of the present invention is not limited. The sunscreen cosmetic of the present invention is mixed with other cosmetic ingredients with a conventional method to prepare a sunscreen cosmetic product such as an oil-in-water emulsified composition, a water-in-oil emulsified composition, and an aqueous solution composition. The aqueous solution sunscreen cosmetic is particularly superior in terms of a freshing texture upon use and a refreshing sensation as well.

EXAMPLES

The invention is described in specific detail through Examples below, but the present invention is not limited to these Examples. The blend ratios are in weight-percentage units unless specified otherwise.

The effect data of the present invention is described below.

Example 1

Regarding Data in FIG. 1 (Data With/Without Addition of the Agar Microgel)

Agar (AX-100 from Ina Food Industries Co., Ltd.) was heated and dissolved, and crushed with a homomixer with a conventional method to prepare an agar microgel containing 1 wt % of agar. Aqueous solutions of Example 1, which contained the agar microgel, and Comparative Example 1, which did not contain it, were prepared. 2 mg/cm$^2$ of the prepared aqueous solution was applied on a quartz plate and a spectrophotometer (U-4100 from Hitachi, Ltd.) was used to measure the ultraviolet absorbance spectra.

The results are shown in FIG. 1. Example 1, which contained the agar microgel, showed a dramatic increase in the ultraviolet absorption effect (absorbance ABS).

Example 1

Aqueous Solution Type Sunscreen Cosmetic

| | |
|---|---|
| Phenylbenzimidazolesulfonic acid (abbreviated as PBSA) | 1 wt % |
| Triethanolamine | 0.6 |
| Agar microgel (agar concentration 1 wt %) | 50 |
| Water | Balance |

Comparative Example 1

Sunscreen Cosmetic Without Agar Microgel

| | |
|---|---|
| Phenylbenzimidazolesulfonic acid (abbreviated as PBSA) | 1 wt % |
| Triethanolamine | 0.6 |
| Water | Balance |

Example 2

Figure 2:
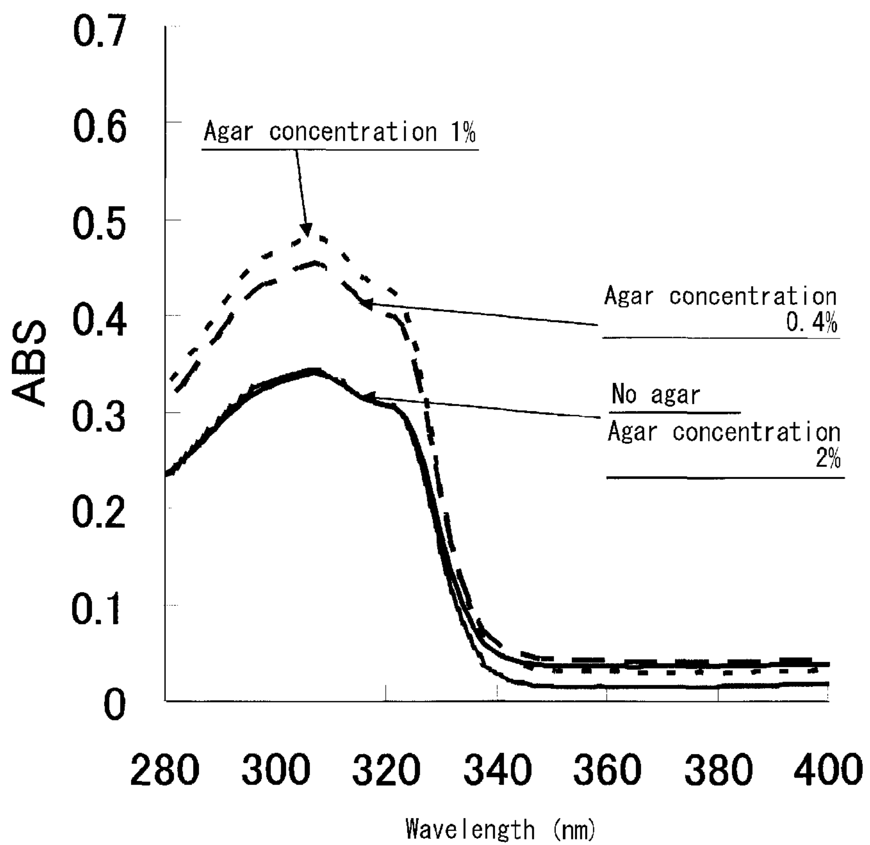
FIG. 2 is an ultraviolet absorption spectrum showing that an agar concentration in the microgel increases the ultraviolet absorption effect. The water soluble ultraviolet absorbent is the same one as in the FIG. 1.

Regarding Data in FIG. 2 (Data of the Agar Concentration in the Agar Microgel)

As in Example 1, the agar concentration in the agar microgel was changed to 0.4 wt %, 1 wt %, and 2 wt % to investigate the ultraviolet absorption effect. Agar microgels having different agar concentrations were prepared and the agar microgels were added in the same way as in Example 1 to prepare Example 2. Also, Comparative examples containing agar microgel were prepared.

The results indicate that the ultraviolet absorption effect around 280-340 nm dramatically increases when the agar concentration is 0.4-1 wt %. However, when the agar concentration was 2 wt %, the result was almost the same as the case where there was no added agar microgel and no increase in the ultraviolet absorption effect was observed. That is, in the present invention, the agar concentration that dramatically increases the ultraviolet absorption effect is, relative to the total amount of the agar microgel, 0.4-1 wt %.

Example 2

Aqueous Solution Type Sunscreen Cosmetic

| | |
|---|---|
| Phenylbenzimidazolesulfonic acid (abbreviated as PBSA) | 1 wt % |
| Triethanolamine | 0.6 |
| Agar microgel (agar concentration 0.4, 1, or 4 wt %) | 50 |
| Water | Balance |

3. Example 3

Figure 3:
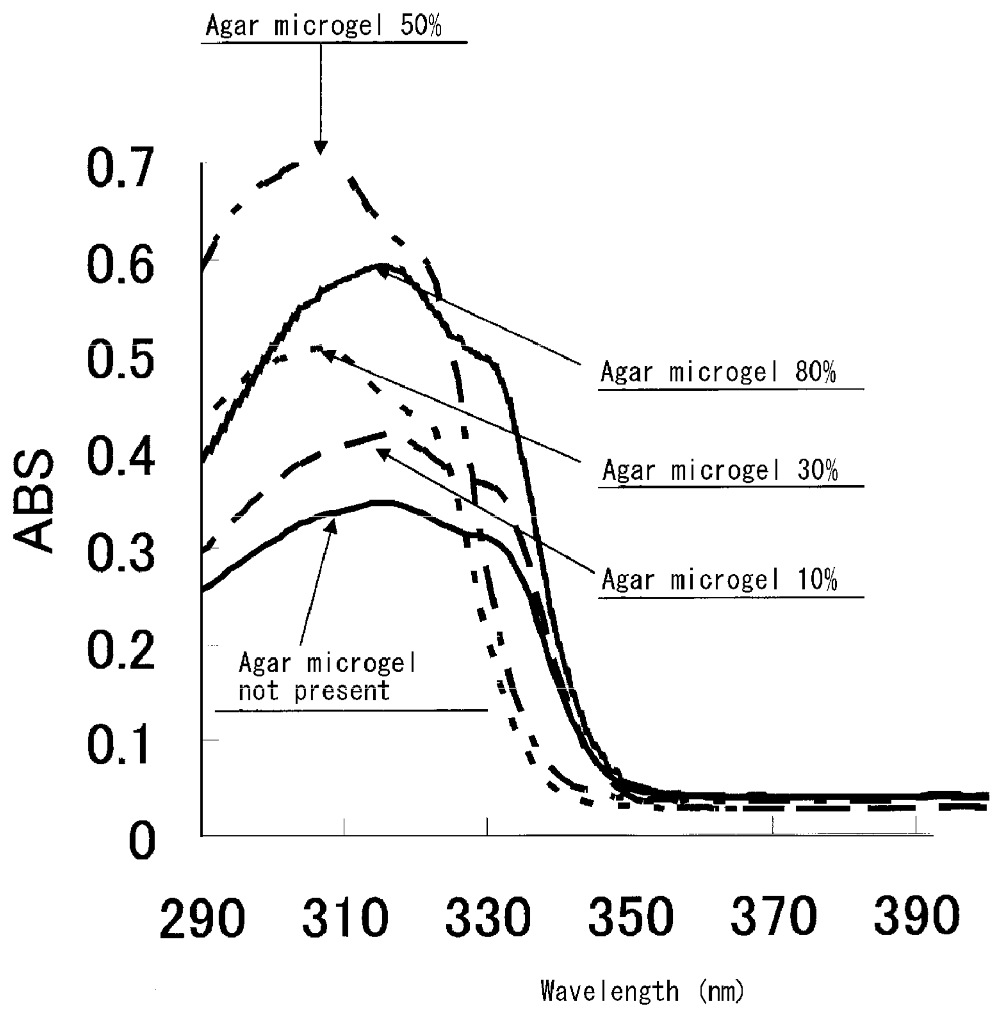
FIG. 3 is an ultraviolet absorption spectrum showing that the ultraviolet absorption effect increases and changes depending on the concentration of the agar microgel in the sunscreen cosmetic. The water soluble ultraviolet absorbent is the same one as in the FIG. 1.

Regarding Data in FIG. 3 (Data of the Blend Ratio of the Agar Microgel)

The blend ratio of agar microgel in the formulation was changed to 10, 30, 50, and 80 wt % and the ultraviolet absorption effect was measured in the same manner as in Example 1. The agar concentration in the agar microgel was 1 wt %.

In every case, the ultraviolet absorption effect increased dramatically compared with when the agar microgel was not blended in. However, as shown in FIG. 3, the maximum ultraviolet absorption effect was achieved at 50 wt %, indicating that it does not necessarily depend just on the agar microgel concentration. A specific increase in the ultraviolet absorption effect was observed in each of the 10-80 wt % cases, but 30-80 wt % is preferable, and the most preferable results were obtained at 50-80 wt %.

Example 3

Aqueous Solution Type Sunscreen Cosmetic

| | |
|---|---|
| Phenylbenzimidazolesulfonic acid (abbreviated as PBSA) | 1 wt % |
| Triethanolamine | 0.6 |
| Agar microgel (agar concentration 1.0 wt %) (The blend ratio 0, 10, 30, 50, or 80) | 0-80 |
| Water | Balance |

Example 4

Figure 4:
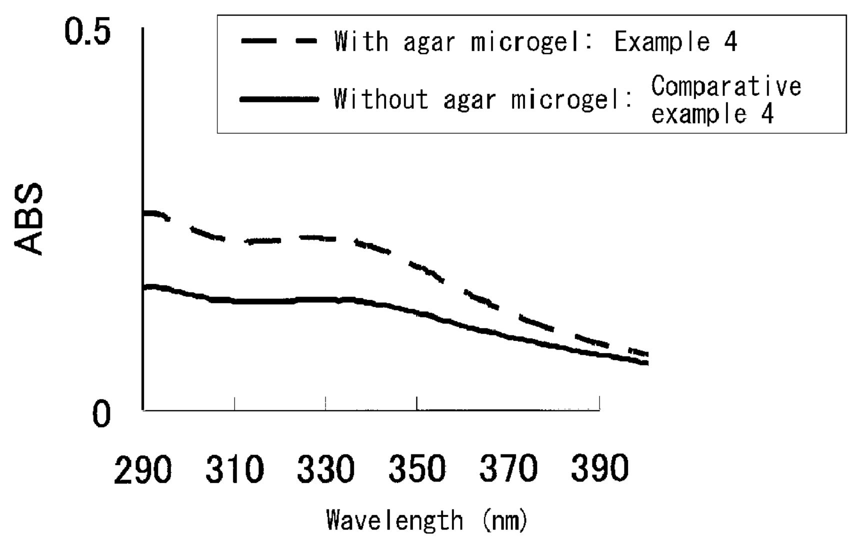
FIG. 4 is an ultraviolet absorption spectrum showing that an agar microgel increases the ultraviolet absorption effect. The water soluble ultraviolet absorbent is 2-hydroxy-4-methoxybenzophenonsulfonic acid.

Data of FIG. 4 (Data With/Without the Addition of the Agar Microgel: a Water Soluble Ultraviolet Absorbent Different From That of Example 1 was Used.)

Agar (AX-100 from Ina Food Industries Co., Ltd.) was heated and dissolved in water, and a conventional method was used to prepare an agar microgel containing 1 wt % of agar. Solutions of Example 4, to which the agar microgel was added, and Comparative example 4, to which the agar microgel was not added, were prepared (aqueous solution type sunscreen cosmetic). As in Example 1, the ultraviolet absorption spectra were investigated.

The results are shown in FIG. 4. Example 4, which contained the agar microgel, showed a dramatic increase in the ultraviolet absorption effect (absorbance ABS).

Example 4

Aqueous Solution Type Sunscreen Cosmetic

| | |
|---|---|
| Sodium 2-hydroxy-4-methoxybenzophenonsulfonate (Abbreviated as ALS24S) | 1 wt % |
| Agar microgel (agar concentration 1.0 wt %) | 50 |
| Water | Balance |

Comparative Example 4

Sunscreen Cosmetic Without Agar Microgel

| | |
|---|---|
| Phenylbenzimidazolesulfonic acid (abbreviated as PBSA) | 1 wt % |
| Water | Balance |

(5) Data of the Tactile Sensation (Freshing Texture) Upon Use

Usig the following formulation (oil-in-water sunscreen cosmetic), the relationship between the blend ratio of the oil soluble ultraviolet absorbent and freshing texture was investigated. The results indicated that the tactile sensation upon use (freshing texture) is superior when the oil soluble ultraviolet absorbent is not blended in. Even when it is blended in for some reason, a preferable blend ratio is 0.5-1% from the point of view of the tactile sensation upon use.

Formulation: Example 5

TABLE 1

| | Raw material | Blend ratio |
|---|---|---|
| Water | Ion-exchanged water | Balance |
| Alcohol | 95 ethyl alcohol, synthesized | 5 |
| Humectant | Dipropylene glycol | 5 |
| | Dynamite glycerin | 3 |
| Thickener | Alkyl-modified carboxyvinyl polymer | 0.1 |
| | Carboxyvinyl polymer | 0.3 |
| | 1% agar microgel | 50 |
| Neutralizer | Triethanolamine | 0.3 |
| Oil soluble UV absorbent | Octylmethoxy cinnamate | * Table 2 |
| Water soluble UV absorbent | Phenylbenzimidazolesulfonic acid | 3 |
| | 2-hydroxy-4-methoxybenzophenonsulfonic acid | 2 |
| Chelating agent | Edetate | 0.02 |
| Preservative | Phenoxy ethanol | 0.5 |

<Results>

TABLE 2

| | Blend ratio of the oil soluble UV absorbent * | | | | |
|---|---|---|---|---|---|
| | 0% | 0.50% | 1% | 3% | 5% |
| Tactile sensation upon use (freshing texture) | ◎ | ○ | ○Δ | Δ | X |

<Evaluation criteria> The aforementioned tactile sensation upon use was evaluated based on the following.

A panel of ten people used the aforementioned sample and the evaluation of the tactile sensation upon use was conducted.

◎: Nine or more reported it was freshing texture.

○: Seven or eight reported it was freshing texture.

○Δ: Five or six reported it was freshing texture.

Δ: Three or four reported it was freshing texture.

X: 0-2 reported it was freshing texture.

The following are formulation examples of the sunscreen cosmetic of the present invention. Each of them is a sunscreen cosmetic that is superior in terms of the ultraviolet absorption properties and the tactile sensation upon use.

Example 6

Sun Screen (Aqueous Solution System)

| Ingredient | wt % |
|---|---|
| 1. Agar | 0.5 |
| 2. Ion-exchanged water | 50 |
| 3. Glycerin | 1 |
| 4. 1,3-butylene glycol | 5 |
| 5. Sodium hexametaphosphate | 0.03 |
| 6. Trimethyl glycine | 1 |
| 7. Poly (sodium aspartate) | 0.1 |
| 8. Potassium alpha-tocpherol 2-L-ascorbate phosphate | 0.1 |
| 9. Thiotaurine | 0.1 |
| 10. Green tea extract | 0.1 |
| 11. Western mint extract | 0.1 |
| 12. Iris root extract | 0.1 |
| 13. Trisodium EDTA | 0.1 |
| 14. Purified water | Balance |
| 15. Ethyl alcohol | 5 |
| 16. POE, POP decyltetradecyl ether | 0.2 |
| 17. Phenoxyethanol | Appropriate amount |
| 18. Perfume | Appropriate amount |
| 19. Phenylbenzimidazolesulfonic acid | 3 |
| 20. Triethanolamine | 1.5 |

Preparation Method:

(1) 1 and 2 are heated and dissolved, and cooled down to room temperature, followed by crushing with a homomixer.

(2) 3-14 are mixed into the (1) part at room temperature.

(3) 15-18 are mixed at room temperature and added to the (1) part.

(4) 19 and 20 are added to the (1) part at room temperature to obtain the target substance.

Example 7

Lotion (Micro Emulsion) (Aqueous Solution System)

| Ingredient | wt % |
|---|---|
| 1. Agar | 0.5 |
| 2. Ion-exchanged water | 50 |
| 3. Ethanol | 10 |
| 4. Dipropylene glycol | 1 |
| 5. Polyethylene glycol 1000 | 1 |
| 6. Polyoxyethylene methylglycoside | 1 |
| 7. Jojoba oil | 0.01 |
| 8. Glyceryl tri-2-ethylhexanoate | 0.1 |
| 9. Polyoxyethylene hydrogenated castor oil | 0.2 |
| 10. Polyglyceryl diisostearate | 0.15 |
| 11. Sodium N-stearoyl-L-glutamate | 0.1 |
| 12. Citric acid | 0.05 |
| 13. Sodium citrate | 0.2 |
| 14. Potassium hydroxide | 0.4 |
| 15. Dipotassium glycyrrhizinate | 0.1 |
| 16. Arginine hydrochloride | 0.1 |
| 17. L-ascorbic acid glucoside | 2 |
| 18. Ogon extract | 0.1 |
| 19. Creeping saxifrage extract | 0.1 |
| 20. Dead-nettle extract | 0.1 |
| 21. Tranexamic acid | 1 |
| 22. Trisodium edetate | 0.05 |
| 23. 2-ethylhexyl-paramethoxycinnamate | 0.01 |
| 24. Dibutylhydroxytoluene | Appropriate amount |
| 25. Paraben | Appropriate amount |
| 26. Deep-ocean water | 3 |
| 27. Purified water | Balance |
| 28. Perfume | Appropriate amount |
| 29. Phenylbenzimidazolesulfonic acid | 3 |
| 30. Triethanolamine | 1.5 |

Preparation Method:

(1) 1 and 2 are heated and dissolved, and cooled down to room temperature, followed by crushing with a homomixer.

(2) 3-11, 23-25, and 27 are heated and dissolved at 70° C.

(3) 12-22, 26, 28, 29, and 30 are mixed and dissolved at RT and added to the (1) part to obtain the target substance.

Example 8

Sunscreen Emulsion (Oil-In-Water Emulsified Cosmetic)

| Ingredient | wt % |
|---|---|
| 1. Agar | 0.5 |
| 2. Ion-exchanged water | 50 |
| 3. Carboxyvinyl polymer | 0.1 |
| 4. Potassium hydroxide | Appropriate amount |
| 5. Dimethylpolysiloxane | 2 |
| 6. Behenyl alcohol | 1 |
| 7. Batyl alcohol | 0.5 |
| 8. Squalane | 6 |
| 9. Pentaerythritol tetra-2-ethylhexanoate | 2 |
| 10. Polyoxyethylene glyceryl isostearate | 1 |
| 11. Polyoxyethylene glycerol monostearate | 1 |
| 12. Hydrogenated oil | 3 |
| 13. Glycerin | 5 |
| 14. 1,3-butylene glycol | 7 |
| 15. Erythritol | 2 |

-continued

| Ingredient | wt % |
|---|---|
| 16. Sodium hexametaphosphate | 0.05 |
| 17. Phenoxyethanol | Appropriate amount |
| 18. Sodium 2-hydroxy-4-methoxybenzo-phenonsulfonate | 1 |
| 19. Purified water | Balance |

Preparation method:

(1) 1 and 2 are heated and dissolved, and cooled down to room temperature, followed by crushing with a homomixer.

(2) 3 and 4 are mixed into the (1) part.

(3) 5-12 are heated and dissolved, which is added to the (1) part and emulsified with a homomixer.

(4) 13-19 are added to the (1) part to obtain the target substance.

Example 9

Sunscreen Emulsion (Oil-In-Water Emulsified Cosmetic)

| Ingredient | wt % |
|---|---|
| 1. Agar | 0.5 |
| 2. Ion-exchanged water | 50 |
| 3. Alkyl acrylate/methacrylate copolymer (Pemulen TR-1) | 0.1 |
| 4. Potassium hydroxide | 0.05 |
| 5. Dimethylpolysiloxane | 3 |
| 6. Decamethylcyclopentasiloxane | 4 |
| 7. Squalane | 2 |
| 8. Sunflower oil | 1 |
| 9. Ethanol | 5 |
| 10. Glycerin | 6 |
| 11. 1,3-butylene glycol | 5 |
| 12. Polyoxyethylene methylglycoside | 3 |
| 13. Sodium hexametaphosphate | 0.05 |
| 14. Hydroxypropyl-beta-cyclodextrin | 0.1 |
| 15. Dipotassium glycyrrhizinate | 0.05 |
| 16. Loquat leaf extract | 0.1 |
| 17. Sodium L-glutamate | 0.05 |
| 18. Fennel extract | 0.1 |
| 19. Yeast extract | 0.1 |
| 20. Lavender oil | 0.1 |
| 21. *Rehmannia* extract | 0.1 |
| 22. Xanthan gum | 0.1 |
| 23. Red iron oxide | Appropriate amount |
| 24. Yellow iron oxide | Appropriate amount |
| 25. Paraben | Appropriate amount |
| 26. Purified water | Balance |
| 27. 2-hydroxy-4-methoxybenzophenonsulfonic acid | 1 |
| 28. Triethanolamine | 0.6 |

Preparation Method:

(1) 1 and 2 are heated and dissolved, and cooled down to room temperature, followed by crushing with a homomixer.

(2) 3 and 4 are added into the (1) part and mixed.

(3) 8-28 are added to the (1) part at room temperature and mixed.

(4) 5-7 are added to the (1) part at room temperature and emulsified with a homomixer to the target substance.

Example 10

Sunscreen Emulsion (Oil-In-Water Emulsified Cosmetic)

| Ingredient | wt % |
|---|---|
| 1. Agar | 0.5 |
| 2. Ion-exchanged water | 50 |
| 3. Bentonite | 1 |
| 4. Stearic acid | 1 |
| 5. Palmitic acid | 1 |
| 6. Glyceryl tri-2-ethylhexanoate | 3 |
| 7. Cetyl 2-ethylhexanoate | 2 |
| 8. Polyoxyethylene glyceryl ethylene isostearate | 1 |
| 9. Glyceryl monostearate | 1 |
| 10. Polyoxyethylene glycerol monostearate | 1 |
| 11. 4-t-butyl-4'-methoxybenzoylmethane | 1 |
| 12. 2-ethylhexyl-paramethoxycinnamate | 7 |
| 13. Eicosene/polyvinylpyrrolidone | 2 |
| 14. Fine particle titanium oxide (30 nm) | 2 |
| 15. Sodium hexametaphosphate | 0.1 |
| 16. Phenoxyethanol | Appropriate amount |
| 17. Trisodium edetate | Appropriate amount |
| 18. Dipropylene glycol | 5 |
| 19. Purified water | Balance |
| 20. Perfume | Appropriate amount |
| 21. Phenylbenzimidazolesulfonic acid | 3 |
| 22. Triethanolamine | 1.5 |

Preparation Method:

(1) 1 and 2 are heated and dissolved, and cooled down to room temperature, followed by crushing with a homomixer.

(2) 3 is added into the (1) part and dispersed with a homomixer at room temperature.

(3) 4-13 are heated and dissolved, which is added to the (1) part and emulsified with a homomixer.

(4) 14 and 15 are added to the (1) part and dispersed with a homomixer.

(5) 16-22 are added to the (1) part at room temperature and emulsified with a homomixer to the target substance.

INDUSTRIAL APPLICABILITY

The present invention is a sunscreen cosmetic that has an excellent ultraviolet absorption effect even when no substantial amount of an oil soluble ultraviolet absorbent is used. Furthermore, it is a sunscreen cosmetic that gives a freshing preferable texture upon use.

The invention claimed is:

1. A sunscreen cosmetic comprising:

relative to the total amount of the sunscreen cosmetic, 10-80 wt % of an agar micro gel wherein the agar content in the agar micro gel is 0.4-1 wt % in a water or water solution based gel; and 0.1-5 wt % of a water soluble ultraviolet absorbent, said water soluble ultraviolet absorbent being phenylbenzimidazole sulfonic acid wherein said sunscreen cosmetic has a higher UV light absorption capacity per unit amount of said ultraviolet absorbent than that of said water soluble ultraviolet absorbent alone.

2. The sunscreen cosmetic of claim 1 comprising, relative to the total amount of the sunscreen cosmetic, 1 wt % or less of an oil soluble ultraviolet absorbent.

3. The sunscreen cosmetic of claim 1, comprising no oil soluble ultraviolet absorbent.

4. A method of manufacturing a sunscreen cosmetic in which an agar micro gel is obtained by dissolving agar in water as stirring and heating are conducted, followed by cooling, the agar content in the agar gel is 0.4-1 wt %, after the dissolution and cooling said agar gel is crushed with a homomixer down to approximately 10-400 micrometers to obtain an agar micro gel, and then a sunscreen cosmetic is manufactured by blending, relative to the total amount of the sunscreen cosmetic, 10-80 wt % of the obtained agar micro gel and, relative to the total amount of the sunscreen cosmetic, 0.1-5 wt % of phenylbenzimidazole sulfonic acid into a cosmetic base agent for being combined with other cosmetic agents.

5. The sunscreen cosmetic composition of claim 1,
- wherein said agar micro gel is made from a 0.4-1 wt % agar in a water or water solution based agar gel, and said sunscreen cosmetic composition is substantially free of emulsifier agent and emulsions.

6. The sunscreen cosmetic composition of claim 1, further comprising:
- an oil component; and
- an oil-in-water emulsifier agent; and
- wherein said agar micro gel is made from a 0.4-1 wt % agar in a water or water solution based agar gel, and said sunscreen cosmetic composition is an oil-in-water emulsified sunscreen cosmetic composition.

7. A method for increasing the LTV light absorption capacity of phenylbenzimidazole sulfonic acid, comprising the steps of:
- preparing a 0.4-1 wt % agar gel in water;
- homogenizing said agar gel into a mixture of a micro-gel of approximately 10-400 micrometers;
- blending said micro-gel in an amount of 10-80 wt % with 0.1-5 wt % of phenylbenzimidazole sulfonic acid to provide a ultraviolet absorbent base; and
- wherein said UV-light absorbent base has a higher ultraviolet light absorption capacity per unit amount than that of said water soluble ultraviolet absorbent alone.

8. The sunscreen cosmetic of claim 1, wherein said agar micro gel is made from 0.4-1% wt. of agarose gel.

9. The sunscreen cosmetic of claim 1, further comprising 2-hydroxy-4-methoxybenzophenonsulfonic acid.

* * * * *